United States Patent
Xie et al.

(10) Patent No.: US 10,548,993 B2
(45) Date of Patent: Feb. 4, 2020

(54) METAL-ENCAPSULATED CARBONACEOUS DOTS

(71) Applicant: UNIVERSITY OF GEORGIA RESEARCH FOUNDATION, INC., Athens, GA (US)

(72) Inventors: Jin Xie, Athens, GA (US); Hongmin Chen, Athens, GA (US); Geoffrey D. Wang, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 441 days.

(21) Appl. No.: 15/500,691

(22) PCT Filed: Jul. 30, 2015

(86) PCT No.: PCT/US2015/042787
§ 371 (c)(1),
(2) Date: Jan. 31, 2017

(87) PCT Pub. No.: WO2016/019090
PCT Pub. Date: Feb. 4, 2016

(65) Prior Publication Data
US 2017/0216464 A1 Aug. 3, 2017

Related U.S. Application Data

(60) Provisional application No. 62/031,821, filed on Jul. 31, 2014.

(51) Int. Cl.
*A61B 5/00* (2006.01)
*A61K 49/18* (2006.01)
(Continued)

(52) U.S. Cl.
CPC ........ *A61K 49/1866* (2013.01); *A61B 5/0035* (2013.01); *A61B 5/0071* (2013.01);
(Continued)

(58) Field of Classification Search
CPC ..... A61B 5/0035; A61B 5/0071; A61B 5/055; A61K 49/1827; A61K 49/1866; G01R 33/5601
See application file for complete search history.

(56) References Cited

U.S. PATENT DOCUMENTS 7,887,771 B2    2/2011   Sun et al.
2002/0127224 A1  9/2002  Chen et al.
(Continued)

FOREIGN PATENT DOCUMENTS

WO    2007095454 A2    8/2007

OTHER PUBLICATIONS

Non-Final Office Action issued in U.S. Appl. No. 15/361,784, dated Jan. 25, 2018.
(Continued)

*Primary Examiner* — George Manuel
(74) *Attorney, Agent, or Firm* — Meunier Carlin & Curfman LLC

(57) ABSTRACT

Nanoparticles described as metal-encapsulated carbonaceous dots or M@C-dots are disclosed. Also disclosed are specific M@C-dots with gadolinium, so called Gd@C-dots. These nanoparticles are biologically inert and preclude the release of metal in biological environments. In addition, despite a dimension exceeding the commonly recognized threshold for renal clearance, the disclosed nanoparticles can be efficiently cleared via urine after systematic injection. Methods of making and using such nanoparticles are also disclosed.

20 Claims, 8 Drawing Sheets

(51) Int. Cl.
A61B 5/055 (2006.01)
G01R 33/56 (2006.01)
(52) U.S. Cl.
CPC .......... A61B 5/055 (2013.01); A61K 49/1827 (2013.01); G01R 33/5601 (2013.01)

(56) References Cited

U.S. PATENT DOCUMENTS

| | | | |
|---|---|---|---|
| 2003/0053951 A1* | 3/2003 | Tartaglia | A61K 49/0002 424/9.2 |
| 2007/0178308 A1* | 8/2007 | Furusawa | B82Y 15/00 428/403 |
| 2012/0323112 A1* | 12/2012 | Jokerst | A61K 49/225 600/420 |
| 2013/0112605 A1 | 5/2013 | Wyndham et al. | |
| 2013/0289520 A1 | 10/2013 | Febvay et al. | |
| 2014/0044648 A1 | 2/2014 | Perez et al. | |

OTHER PUBLICATIONS

International Preliminary Report on Patentability issued in PCT/US15/36391, dated Dec. 26, 2016.
International Preliminary Report on Patentability issued in PCT/US15/42787, dated Feb 9, 2017.
International Search Report and Written Opinion, issued in PCT/US15/36391, dated Sep. 23, 2015.
International Search Report and Written Opinion, issued in PCT/US15/42787, dated Oct. 29, 2015.
Abada, et al., "Highly relaxing gadolinium based MRI contrast agents responsive to Mg2+ sensing", Chem. Comm. 2012, 48, 4085-4087.
Aime, et al., "Biodistribution of Gadolinium-Based Contrast Agents, Including Gadolinium Deposition", J. Magn. Reson. Imaging 2009, 30, 1259-1267.
Barge, et al., "How to determine free Gd and free ligand in solution of Gd chelates. A technical note", Cont. Media Mol. Imaging, 2006, 1, 184-188.
Bhunia, et al., "Carbon Nanoparticle-Based Fluorescent Bioimaging Probes", Sci. Rep. 2013, 3, 7 pages.
Bolskar, et al., "First Soluble M@C60 Derivatives Provide Enhanced Access to Metallofullerenes and Permit in Vivo Evaluation of Gd@C60[C(COOH)2]10 as a MRI Contrast Agent", J. Am. Chem. Soc. 2003, 125, 5471-5478.
Bridot, et al., "Hybrid Gadolinium Oxide Nanoparticles: Multimodal Contrast Agents for in Vivo Imaging", J. Am. Chem. Soc. 2007, 129, 5076-5084.
Caravan, et al., "Gadolinium(III) Chelates as MRI Contrast Agents: Structure, Dynamics, and Applications", Chem. Rev. 1999, 99, 2293-2352.
Caravan, et al., "Collagen-Targeted MRI Contrast Agent for Molecular Imaging of Fibrosis", Angew. Chem. Int. Ed. 2007, 46, 8171-8173.
Casey, et al., "Sensors and regulators of intracellular pH", Nature Rev. Molec. Cell Bio. 2010, 11, 50-61.
Chen, et al., "Nanoparticles for Improving Cancer Diagnosis", Mater. Sci. Eng. R Rep., 2013, 74, 35-69.
Chen, et al., "Hollow/Rattle-Type Mesoporous Nanostructures by a Structural Difference-Based Selective Etching Strategy", ACS Nano 2010, 4, 529-539.
Chen, et al., "Reversible Pore-Structure Evolution in Hollow Silica Nanocapsules: Large Pores for siRNA Delivery and Nanoparticle Collecting", Small 2011, 7, 2935-2944.
Chen, et al., "Label-Free Luminescent Mesoporous Silica Nanoparticles for Imaging and Drug Delivery", Theranostics 2013, 3, 650-657.
Chen, et al., "Gd-Encapsulated Carbonaceous Dots with Efficient Renal Clearance for Magnetic Resonance Imaging", Adv. Mater. 2014, 26, 6761-6766.
Chrysochou, et al., "Low Risk for Nephrogenic Systemic Fibrosis in Nondialysis Patients Who Have Chronic Kidney Disease and Are Investigated with Gadolinium-Enhanced Magnetic Resonance Imaging", Clin. J. Am. So.c Nephro. 2010, 5, 484-489.
Corot, et al., "Structure-activity relationship of macrocyclic and linear gadolinium chelates: Investigation of transmetallation effect on the zinc-dependent metallopeptidase angiotensin-converting enzyme", J. Magn. Reson. Imaging 1998, 8, 695-702.
Dong, et al., "Carbon-Based Dots Co-doped with Nitrogen and Sulfur for High Quantum Yield and Excitation-Independent Emission", Angew. Chem. Int. Ed. 2013, 52, 7800-7804.
Ersoy, et al., "Biochemical Safety Profiles of Gadolinium-Based Extracellular Contrast Agents and Nephrogenic Systemic Fibrosis", J. Magn. Reson. Imaging. 2007, 26, 1190-1197.
Graf, et al., "Surface Functionalization of Silica Nanoparticles Supports Colloidal Stability in Physiological Media and Facilitates Internalization in Cells", Langmuir 2012, 28, 7598-7613.
Holt, et al., "Subcellular Partitioning and Analysis of Gd3+-Loaded Ultrashort Single-Walled Carbon Nanotubes", ACS Appl. Mater. Interfaces 2015, 7, 14593-14602.
Huang, et al., "Effects of Nanoparticle Size on Cellular Uptake and Liver MRI with Polyvinylpyrrolidone-Coated Iron Oxide Nanoparticles", ACS Nano 2010, 4, 7151-7160.
Huang, et al., "Multifunctional Metal Rattle-Type Nanocarriers for MRI-Guided Photothermal Cancer Therapy", Mol. Pharmaceut. 2014, 11, 3386-3394.
Kalavagunta, et al., "In vitro Gd-DTPA relaxometry studies in oxygenated venous human blood and aqueous solution at 3 and 7 T", Contrast Media Mol. Imaging 2014, 9, 169-176.
Kim, et al., "Mesoporous Silica-Coated Hollow Manganese Oxide Nanoparticles as Positive T1 Contrast Agents for Labeling and MRI Tracking of Adipose-Derived Mesenchymal Stem Cells", J. Am. Chem. Soc. 2011, 133, 2955-2961.
Laus, et al., "Understanding Paramagnetic Relaxation Phenomena for Water-Soluble Gadofullerenes", J. Phys. Chem. C 2007, 111, 5633-5639.
Lee, et al., "Paramagnetic inorganic nanoparticles as T1 MRI contrast agents", WIREs Nanomed. Nanobiotechnol. 2014, 6, 196-209.
Lim, et al., "Gadolinium-coordinated elastic nanogels for in vivo tumor targeting and imaging", Biomaterials 2013, 34, 6846-6852.
Lim, et al., "Carbon quantum dots and their applications", Chem. Soc. Rev. 2015, 44, 362-381.
Lingam, et al., "Evidence for Edge-State Photoluminescence in Graphene Quantum Dots", Adv. Funct. Mater. 2013, 23, 5062-5065.
Liu, et al., "Facile Synthetic Method for Pristine Graphene Quantum Dots and Graphene Oxide Quantum Dots: Origin of Blue and Green Luminescence", Adv. Mater. 2013, 25, 3657-3662.
Luo, et al., "Carbon "quantum" dots for optical bioimaging", J. Mater. Chem. B 2013, 1, 2116-2127.
Meloni, et al., "Safety of cardiovascular magnetic resonance gadolinium chelates contrast agents in patients with hemoglobinopathies", Haematologica 2009, 94, 1625-1627.
Miao, et al., "Recent advances in carbon nanodots: synthesis, properties and biomedical applications", Nanoscale 2015, 7, 1586-1595.
Na, et al., "Inorganic Nanoparticles for MRI Contrast Agents", Adv. Mater. 2009, 21, 2133-2148.
Pan, et al., "Hydrothermal Route for Cutting Graphene Sheets into Blue-Luminescent Graphene Quantum Dots", Adv. Mater. 2010, 22, 734-738.
Ren, et al., "Facile Preparation of Gadolinium (III) Chelates Functionalized Carbon Quantum Dots-based Contrast Agent for Magnetic Resonance/Fluorescence Multimodal Imaging", J. Mat. Chem. B 2014, 1-3, 10.
Sancey, et al., "Long-Term in Vivo Clearance of Gadolinium-Based AGuIX Nanoparticles and Their Biocompatibility after Systemic Injection", ACS Nano 2015, 9, 2477-2488.
Shu, et al., "Facile Preparation of a New Gadofullerene-Based Magnetic Resonance Imaging Contrast Agent with High 1H Relaxivity", Biocon. Chem. 2009, 20, 1186-1193.
Sitharaman, et al., "Superparamagnetic gadonanotubes are high-performance MRI contrast agents", Chem. Commun. 2005, 3915-3917.

(56) References Cited

OTHER PUBLICATIONS

Sithararnan, et al., "Gadonanotubes as new high-performance MRI contrast agents", Int. J. Nanomed. 2006, 1, 291-295.
Soto-Cantu, et al., "Synthesis and Rapid Characterization of Amine-Functionalized Silica", Langmuir 2012, 28, 5562-5569.
Sun, et al., "Quantum-Sized Carbon Dots for Bright and Colorful Photoluminescence", J. Am. Chem. Soc. 2006, 128, 7756-7757.
Sun, et al., "Doped Carbon Nanoparticles as a New Platform for Highly Photoluminescent Dots", J. Phys. Chem. C 2008, 112, 18295-18298.
Terreno, et al., "Challenges for Molecular Magnetic Resonance Imaging", Chem. Rev. 2010, 110, 3019-3042.
Thirumavalavan, et al., "Preparation and Morphology Studies of Nano Zinc Oxide Obtained Using Native and Modified Chitosans", Mat. 2013, 6, 4198-4212.
Tian, et al., "Nanosized Carbon Particles From Natural Gas Soot", Chem. Mater. 2009, 21, 2803-2809.
Vivero-Escoto, et al., "Biodegradable Polysilsesquioxane Nanoparticles as Efficient Contrast Agents for Magnetic Resonance Imaging", Small 2013, 9, 3523-3531.
Wang, et al., "Highly Luminescent Organosilane-Functionalized Carbon Dots", Adv. Funct. Mater. 2011, 21, 1027-1031.
Wang, et al., "Carbon quantum dots: synthesis, properties and applications", J. Mater. Chem. C 2014, 2, 6921-693.
Wang, et al., "Smart Albumin-Biomineralized Nanocomposites for Multimodal Imaging and Photothermal Tumor Ablation", Adv. Mater. 2015, 27, 3874-3882.
Wu, et al., "Stability and Biodistribution of a Biodegradable Macromolecular MRI Contrast Agent Gd-DTPA Cystamine Copolymers (GDCC) in Rats", Pharm. Res. 2010, 27, 1390-1397.
Xing, et al., "Bioconjugated quantum dots for multiplexed and quantitative immunohistochemistry", Nat. Protoc. 2007, 2, 1152-1165.
Yang, et al., "Carbon Dots for Optical Imaging in Vivo", J. Am. Chem. Soc. 2009, 131, 11308-11309.
Yang, et al., "RGD-Conjugated Nanoscale Coordination Polymers for Targeted T 1- and T 2-weighted Magnetic Resonance Imaging of Tumors in Vivo", Adv. Funct. Mater. 2014, 24, 1738-1747.
Ye, et al., "Integrin Targeting for Tumor Optical Imaging", Theranostics 2011, 1, 102-126.
Zhou, et al., "A Synergistically Enhanced T1-T2 Dual-Modal Contrast Agent", Adv. Mater. 2012, 24, 6223-6228.
Zhou, et al., "Engineered Iron-Oxide-Based Nanoparticles as Enhanced T1 Contrast Agents for Efficient Tumor Imaging", ACS Nano 2013, 7, 3287-3296.
Zhou, et al., "Gadolinium-based contrast agents for magnetic resonance cancer imaging", Wiley Interdiscip. Rev. Nanomed. Nanobiotech. 2013, 5, 1-18.
Zhu, et al., "Surface Chemistry Routes to Modulate the Photoluminescence of Graphene Quantum Dots: From Fluorescence Mechanism to Up-Conversion Bioimaging Applications", Adv. Funct. Mater. 2012, 22, 4732-4740.

Perazella, "Gadolinium-Contrast Toxicity in Patients with Kidney Disease: Nephrotoxicity and Nephrogenic Systemic Fibrosis", Curr. Drug Safety 2008, 3, 1, 67-75.
Perazella, "Nephrogenic Systemic Fibrosis, Kidney Disease, and Gadolinium: Is There a Link?" Clin. J. Am. Soc. Neph. 2007, 2, 200-202.
Thomsen, et al., "Is there a causal relation between the administration of gadolinium based contrast media and the development of nephrogenic systemic fibrosis (NSF)?" Clin. Rad. 2006, 61, 11, 905-906.
Thomsen, "Nephrogenic systemic fibrosis: a serious late adverse reaction to gadodiamide", Eur. Rad. 2006, 16, 12, 2619-2621.
Hellman, "Gadolinium-Induced Nephrogenic Systemic Fibrosis", Sem. Neph. 2011, 31, 3, 310-316.
Cao, et al., "Competitive Performance of Carbon "Quantum" Dots in Optical Bioimaging", Theranostics 2012, 2, 3, 295-301.
Choi, et al., "Design Considerations for Tumor-Targeted Nanoparticles", Nat. Nanotech. 2010, 5, 1, 42-47.
Bourlinos, et al., "Surface functionalized carbogenic quantum dots", Small 2008, 4, 4, 455-458.
Li et al., "Simple and green synthesis of nitrogen-doped photoluminescent carbonaceous nanospheres for bioimaging", Angew. Chem., Int. Ed. 2013, 52, 31, 8151-8255.
Ding, et al., "Functional surface engineering of C-dots for fluorescent biosensing and in vivo bioimaging", Acc. Chem. Res. 2014, 47, 20-30.
Michalet, et al., "Quantum Dots for Live Cells, in Vivo Imaging, and Diagnostics", Science 2005, 307, 5709, 538-544.
Song, et al., "Functional nanoprobes for ultrasensitive detection of biomolecules", Chem. Soc. Rev. 2010, 39, 11, 4234-4243.
Huang, et al., "Gd-based macromolecules and nanoparticles as magnetic resonance contrast agents for molecular imaging", Curr. Top. Med. Chem. 2013, 13, 4, 411-421.
Jokerst, et al., "Nanoparticle PEGylation for imaging and therapy", Nanomedicine 2011, 6, 4, 715-728.
Liu, et al., "Role of liposome size and RES blockade in controlling biodistribution and tumor uptake of GM1-containing liposomes", Biochim. Biophys. Acta. 1992, 1104, 1, 95-101.
Gao, et al., "A Novel Clinically Translatable Fluorescent Nanoparticle for Targeted Molecular Imaging of Tumors in Living Subjects", Nano Lett. 2012, 12, 1, 281-286.
Liu, et al., "Renal clearable inorganic nanoparticles: a new frontier of bionanotechnology", Mater. Today 2013, 16, 12, 477-486.
Wang, et al., "Amphiphilic egg-derived carbon dots: rapid plasma fabrication, pyrolysis process, and multicolor printing patterns", Angew. Chem. Int. Ed. 2012, 51, 37, 9297-9301.
Liu, et al., "Hydrothermal treatment of grass: a low-cost, green route to nitrogen-doped, carbon-rich, photoluminescent polymer nanodots as an effective fluorescent sensing platform for label-free detection of Cu(II) ions", Adv. Mater. 2012, 24, 15, 2037-2041.
Final Office Action issued in U.S. Appl. No. 15/361,784, dated Sep. 21, 2018.

* cited by examiner

METAL-ENCAPSULATED CARBONACEOUS DOTS

ACKNOWLEDGMENT OF GOVERNMENT SUPPORT

This invention was made with government support under Grant No. R00CA153772 awarded by the National Institutes of Health. The government has certain rights in the invention.

FIELD

The subject matter disclosed herein generally relates to nanoparticles containing a metal encapsulated in a carbonaceous shell, and methods of making and using thereof

BACKGROUND

Main Gadolinium(III)-based contrast probes have been widely used in clinical MRI. So far, there are at least nine formulations of Gd-containing contrast agents approved for human use in the U.S., and they are assisting more than 10 million magnetic resonance imaging (MRI) scans per year. Free Gd is known to have a high toxicity profile, hence clinically used Gadolinium agents are all in the form of Gd-chelator complexes. Despite the complexation, however, these contrast agents are found to cause severe nephrogenic systemic fibrosis (NSF), especially for patients with renal diseases or poor renal functions (Perazella, *Curr. Drug Safety* 2008, 3(1):67-75; Chrysochou et al., *Clin. J. Am. Soc. Neph.* 2010, 5(3): 484-489; Perazella et al., *Clin. J. Am. Soc. Neph.* 2007, 2(2):200-202). For this reason, the FDA has issued warnings on the use of several Gd-based contrast agents in patients with kidney dysfunction (Thomsen et al., *Clin. Rad.* 2006, 61(11):905-906; Thomsen, *Eur. Rad.* 2006, 16(12):2619-2621; Hellman, *Sem. Neph.* 2011, 31(3):310-316.5-7). This status underscores the significance of developing alternative contrast agents with more favorable safety profiles.

One approach that has been investigated is to load or imbed Gd(III) into a nanoparticle capsule/carrier that can suppress the Gd release while maintaining the $T_1$-shortening capacity. Examples of this approach include $Gd_2O_3$ nanoparticles (Bridot et al., *J. Am. Chem. Soc.* 2007, 129(16): 5076-5084), Gd-loaded silica nanoparticles (Vivero-Escoto et al., *Small* 2013, 9(20):3523-3531), and Gd-doped $Fe_3O_4$ nanoparticles (Zhou et al., *Adv. Mater.* 2012, 24(46):6223-6228). Due to their relatively large sizes, however, these nanoparticles are mostly accumulated in the reticuloendothelial (RES) organs after injection, most prominently the liver. Subsequent particle degradation may cause slow release of Gd(III) to the surroundings, and the long-term impact is largely unknown. Thus, what are needed are new Gd-based contrast agents that have improved safety profiles. The compositions and methods disclosed herein address these and other needs.

SUMMARY

In accordance with the purposes of the described materials, compounds, compositions, articles, and methods, as embodied and broadly described herein, the subject matter described herein, in one aspect, relates to compositions and methods for preparing and using such compositions. In a further aspect, the disclosed subject matter relates to a nanoparticle comprising a metal encapsulated in an amorphous carbon shell. In particular examples, the disclosed subject matter relates to a nanoparticle comprising gadolinium encapsulated in an amorphous carbon shell. The amorphous carbon shell of the disclosed nanoparticles can comprise carboxyl groups. The average diameter of the disclosed nanoparticle can be from about 2 nm to about 34 nm.

The subject matter described herein also relates to methods of making the disclosed nanoparticles comprise calcining a metal with a chelator. Methods of functionalizing the disclosed nanoparticles are also disclosed. Methods of using the disclosed nanoparticles, e.g., for imaging are also disclosed.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DECRIPTION OF THE FIGURES

The accompanying figures, which are incorporated in and constitute a part of this specification, illustrate several aspects of the disclosure, and together with the description, serve to explain the principles of the disclosure.

FIG. 1 displays characterizations of Gd@C-dots. Panel (a) is a schematic illustration of Gd@C-dots. Panel (b) is a TEM and Panel (c) is a HRTEM image of 12 nm Gd@C-dots. Panel (d) shows elemental mapping (Gd) of Gd@C-dots. Panel (e) is a STEM image of a single 12 nm Gd@C-dot. Panel (f) is an EDX line profile across the nanoparticle in Panel (e). Points "A" and "B" corresponded to those labeled respectively in Panel (e). Panel (g) shows the DLS result of Gd@C-dots. Panel (h) shows the Zeta potential of Gd@C-dots.

FIG. 2 displays the optical and magnetic properties of Gd@C-dots. Panel (a) is the absorption and photoluminescence spectra of Gd@C-dots. Panel (b) shows a photostability study. Gd@C-dots were under continuous irradiation by UV light (30 W, 254 nm) and the photoluminescence (ex/em 360/425 nm) intensity was monitored over time. Panel (c) shows a comparison of photostability among FITC, CdSe/ZnS QDs, and Gd@C-dots. The three solutions were under continuous irradiation by UV light (30 W, 254 nm) for different amounts of time. Panel (d) shows $T_1$-weight MR images of Gd@C-dot agarose samples of different Gd concentrations. Panel (e) shows the linear correlation between $R_1(T_1^{-1})$ and Gd concentration, based on readings from Panel (d). The $r_1$ relaxivity, which is the slope of the curve, was determined to be 5.88 $mM^{-1}s^{-1}$.

FIG. 3 displays cytotoxicity and cell targeting data. Panel (a) shows the photoluminescence intensity (ex/em 360/425 nm) change when Gd@C-dots were incubated in buffers of different pH values. Panel (b) shows Gd release from Gd@C-dots over time. The nanoparticles were incubated in solutions with pH 5 or 7.4. #: The overall Gd concentrations in the solutions. Panel (c) shows cell viability, evaluated by MTT assays with U87MG cells. 2.5 mM Ca(II) was added in the incubation medium. Panel (d) displays a cell targeting study. RGD-Gd@C-dots were incubated with U87MG cells for 30 min and the cells were then imaged under a fluorescence microscope (scale bar, 10 μm). For controls, cells were incubated with Gd@C-dots at the same Gd concentration or with RGD-Gd@C-dots in the presence of free c(RGDyK) (30×). Panel (e) shows $T_1$-weighted MR images of cell pellets, where cells had been incubated with either RGD-Gd@C-dots or Gd@C-dots.

FIG. 4, panel (a), shows $T_1$-weighted MR images acquired at different time points after injection of Gd@C-dots or RGD-Gd@C-dots. Panel (b) shows the signal change in the bladder (bl) and liver (lv), based on region of interest (ROI) analysis on images from panel (a). Panel (c) shows a photoluminescence analysis on urine samples taken 60 min after the injection of RGD-Gd@C-dots.

FIG. 5, panel (a), shows $T_1$-weighted transverse MR images. Gd@C-dots or RGD@C-dots (3.2 mg/kg) were intravenously injected into U87MG tumor bearing mice. Images were acquired at 0, 10, 30, 45, 60 and 240 min. For both types of nanoparticles, strong signals in the bladder were observed soon after the particle injection, indicating fast renal clearance. Panel (b) shows $T_1$-weighted coronal MR images. Significant signal enhancement was observed in tumors of animals injected with RGD@Gd-dots. Panel (c) shows the relative signal change at different time points, based imaging results from panel (b). Panel (d) shows an immunofluorescence histology study with tumor samples. Good overlap was observed between RGD-Gd@C-dots and positive integrin $\beta_3$ staining. As a comparison, Gd@C-dots showed minimal tumor uptake. Red, integrin $\beta_3$ (Cy5); blue, fluorescence from C-dots. Scale bars, 50 μm.

DETAILED DESCRIPTION

Figure 1:
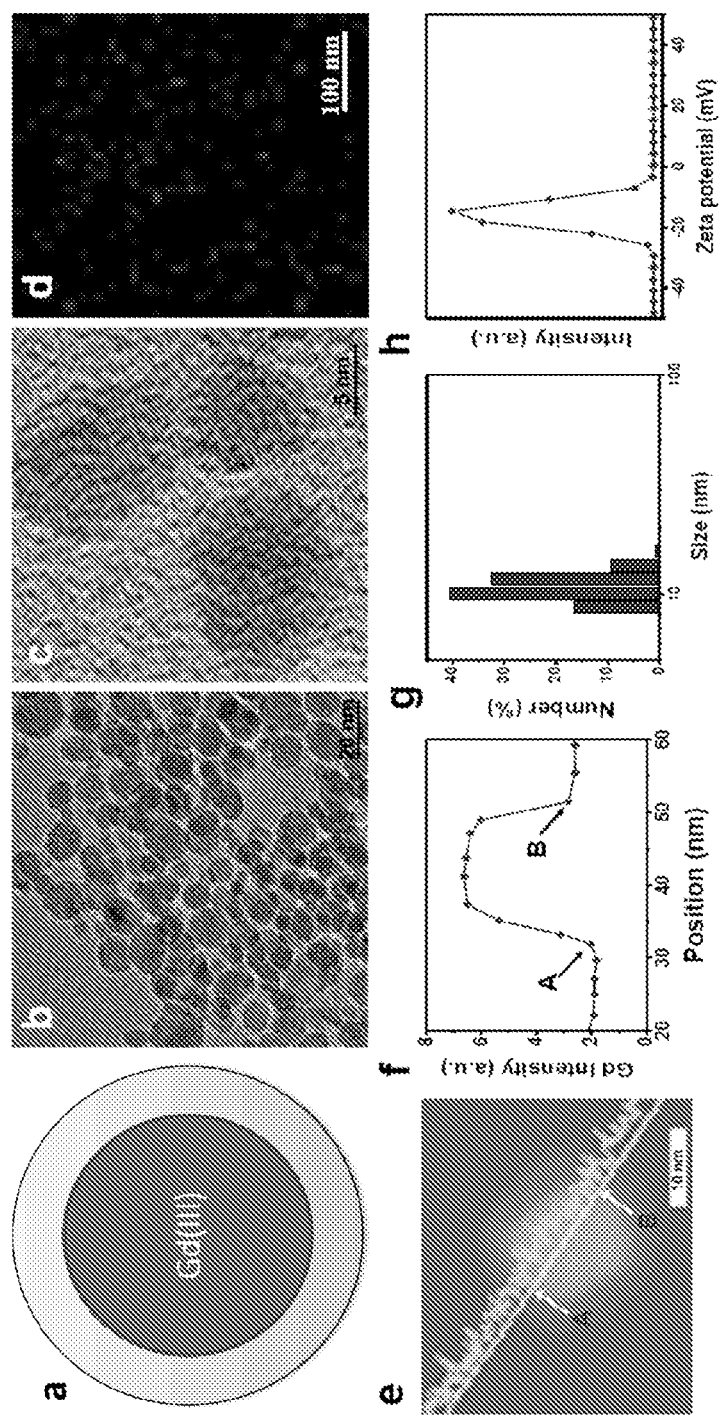

The present disclosure can be understood more readily by reference to the following detailed description and the Examples included therein and to the Figures and their previous and following description.

As used in the specification and the appended claims, the singular forms "a," "an," and "the" include plural referents unless the context clearly dictates otherwise. Thus, for example, reference to "a particle" includes mixtures of two or more such particles, reference to "the compound" includes mixtures of two or more such compositions, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. Unless stated to the contrary "about" a particular value means within 5% of the particular value, e.g., within 2% or 1% of the particular value.

By "amorphous" is meant non-crystalline and without structural order over a long range, e.g., a majority of the nanoparticle. An amorphous shell can contain some ordered structure over a short range atomic length scale, but the majority of the shell is not ordered and non-crystalline.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Compositions

Disclosed herein are nanoparticles where a metal is encapsulated in an amorphous carbon shell. The metal can be pure metal, metal oxide, metal complexes, or mixtures of these. These metal encapsulated carbon dots (herein referred to as M@C-dots) can have a wide variety of uses. In some specific examples, the metal is gadolinium; thus disclosed herein are Gd encapsulated carbon dots (hereafter referred to as Gd@C-dots). Also, reference to M@C-dots herein is meant to specifically include reference to Gd@C-dots.

Unlike most other nanocarriers/nanocapsules, carbon has low-toxicity and is highly biologically inert. Thus, the disclosed nanoparticle M@C-dots can remain intact even in harsh biological environments, therefore precluding the risk of metal release to the surroundings (Cao et al., *Theranostics* 2012, 2(3):295-301). With specific reference to gadolinium, stemming from the inert carbon coating, the disclosed nanoparticles are immune to the issue of Gd leaking that is often observed with complex-based Gd agents. Leakage of other metals from the disclosed nanoparticles is also expected.

The disclosed nanoparticles can have an average size of about 12 nm in diameter. For example, the disclosed nanoparticles can have an average size of from about 2 nm to about 34, from about 4 nm to about 32 nm, from about 6 nm to about 30 nm, from 8 to about 28 nm, from about 10 nm to about 24 nm, from about 12 nm to about 22 nm, from about 14 nm to about 20 nm, from about 26 nm to about 18 nm, from about 8 nm to about 16 nm, from about 10 nm to about 14 nm, from about 12 nm to about 20 nm, or from about 14 nm to about 18 nm. In still other examples, the disclosed nanoparticles can have an average size of 2, 4, 6, 8, 9, 10, 11, 12, 13, 14, 15, 16, 17, 18, 19, 20, 21, 22, 23, 24, 25, 26, 28, 30, 32, or 34 nm, where any of the stated values can form an upper or lower endpoint of a range.

Also, the disclosed nanoparticles, for example, the Gd@C-dots, can have a high $r_1$ relaxivity compared to complex-based Gd reagents. For example, for 12 nm Gd@C-dots, $r_1$ relaxivity is about 5.88 $mM^{-1}s^{-1}$ (on per Gd basis). The $r_1$ relaxivity can be tuned up to 50 $mM^{-1}s^{-1}$ by adjusting the size and composition of Gd@C-dots. Thus, the disclosed Gd@C dots can have $r_1$ relaxivity from about 0 to about 50 $mM^{-1}s^{-1}$, e.g., about 0, 5, 10, 15, 20, 25, 30, 35, 40, 45, or 50 $mM^{-1}s^{-1}$, where any of the stated values can form an upper or lower end point of a range. In specific examples, the disclosed Gd@C-dots can have a $r_1$ relaxivity from about 0 to about 10, from about 5 to about 15, from about 10 to about 20, from about 15 to about 25, from about 20 to about 30, from about 25 to about 35, from about 30 to about 40, from about 35 to about 45, from about 40 to about 50, from about 0 to about 25, or from about 25 to about 50 $mM^{-1}s^{-1}$.

Moreover, the disclosed Gd@C-dots also possess bright photoluminescence, boasting a high quantum yield and excellent photostability that is even superior to quantum dots. The QY is found to be 19.7% for 12 nm Gd@C-dots but can be tuned up to 80% by adjusting the size and composition of Gd@C-dots. The QY of the disclosed Gd@C-dots is comparable to the highest reported QYs of C-dots (Bhunia et al., *Sci. Rep.* 2013, 3, 1473). Notably, however, for most of the previously reported C-dots, a post-synthesis surface passivation step is usually needed to grant particles with strong luminescence (Sun et al., *J. Am. Chem. Soc.* 2006, 128(24):7756-7757; Wang et al., *Angew. Chem. Int. Ed.* 2012, 51(37):9297-9301; Liu et al., *Adv. Mater.* 2012, 24(15):2037-2041). In comparison, the strong luminescence of the Gd@C-dots can be achieved in one-step calcination with no added ligands. In specific examples, the discloed Gd@C-dots can have a QY of from about 0 to about 80, from about 15 to about 65, from about 30 to about 80, from about 0 to about 35, from about 15 to about 75, from about 0 to about 20, or from about 20 to about 35%.

Uniquely, despite having dimensions that can exceed the commonly recognized threshold for renal clearance (about 5.5 nm) (Choi et al., *Nat. Nanotech.* 2010, 5(1):42-47), systematically injected nanoparticle M@C-dots can be efficiently excreted via urine, further minimizing toxicity risks. After systematic injection, it can be desirable that an imaging probe can home efficiently to the diseased area (e.g., a tumor), with the unbound probes rapidly excreted from the host. This can be challenging for nanoparticle-based imaging probes, most of which have a relatively large size, a high tendency of opsonization, and as a result, a high level of liver accumulation (Jokerst et al., *Nanomedicine* 2011, 6(4): 715-728; Liu et al., *Biochim. Biophys. Acta.* 1992, 1104(1): 95-101). Studies showed that when the overall size was below 5.5 nm, nanoparticles could be excreted by renal clearance, thereby avoiding extended durations in the host (Choi et al., *Nat. Nanotech.* 2010, 5(1):42-47). This size criterion, however, is difficult to meet for many nanomaterials, including most Gd-containing nanoparticles under investigation. It is in this sense that the renal clearance of the disclosed Gd@C-dots is particularly significant. Both conjugated RGD-Gd@C-dots and Gd@C-dots have sizes well above the recognized threshold for renal clearance and yet are able to be efficiently excreted via urine. Though not wishing to be bound by theory, it is believed that the unique surface of the disclosed nanoparticles play a role in renal clearance. With a shell made of amorphous carbon but decorated with carboxyl groups, the surface of the disclosed nanoparticles lies between hydrophobic and hydrophilic. This affords the particles with good colloidal stability and still gives them the capacity to cross certain types of biological barriers. It is noted that recently, there was another report by Gao et al. showing that 11.8 nm QDs had efficient renal clearance (Gao et al., *Nano Lett.* 2012, 12(1): 281-286). The authors also attributed the uncommon phenomenon to the surface coating, which in that case was a dendron polymer. Aside from particle dimension, there are surface related parameters that can assist with fast particle excretion.

The disclosed nanoparticles are not endohedral fullerenes, which are much smaller than the disclosed M@C-dots. That is, endohedral fullerenes are usually less than about 1 nm. $C_{60}$, for example, has a diameter of 0.7 nm. Also, the fullerene structure is highly ordered, where as the disclosed nanoparticles have an amorphous shell that functionalized with carboxyl groups.

Conjugates

The surface of the disclosed nanoparticles contains carboxyl groups that can be used to functionalize the surface of the nanoparticles. The carbonyl groups are electrophiles that can be used in nucleophilic substitution reactions or carbodiimide coupling reactions with any desirable functionalizing reagent. In certain examples, the functionalizing reagent can contain a targeting moiety that can be used to direct the functionalized nanoparticles to specific locations in the patient. Thus disclosed herein are M@C-dot nanoparticles functionalized with a targeting moiety. For example, RGD-peptides and cyclic RGD-peptides, when coupled to the disclosed M@C-dots, can direct the nanoparticles to target tumors. Similarly, EGFR targeting peptides, EGFR targeting therapeutics, VEGF targeting peptides, VEGF targeting therapeutics, and the like can be coupled/attached to the disclosed nanoparticles. Different types of antibodies, such as Herceptin, Avastin, and Erbitux, etc., can be coupled to the particle surface for facilitating particle targeting to tumors. Small molecule drugs such as doxorubicin, methotrexate or paclitaxel or their derivatives and can also be coupled to the surface of the nanoparticles, and in these cases the particles are used as drug carriers. Functionalizing the surface of the nanoparticles can also be used to assist the passage of the M@C-dots across certain cell membranes. For instance, the particle surface can be coated with a layer of positively charged polymer such as polyethylenimine and the resulting conjugates can be used as carriers for gene delivery (e.g., siRNA) due to assisting gene therapeutics passing through negatively charged cell membranes.

Suitable reagents for initiating a carbodiimide-mediate coupling to the carboxyl of the disclosed nanoparticles are commercially available. Specific examples of such reagents include, but are not limited to, water soluble carbodiimides such as 1-ethyl-3-(3-dimethylaminopropyl)-carbodiimide hydrochloride and 1-cyclohexyl-3-(2-morpholinoethyl)-carbodiimide-metho-p-toluene sulfonate, alcohol and water soluble N-ethyoxycarbonyl-2-ethoxy-1,2-dihydroquinoline, and organic soluble N,N'-dicyclohexylcarbodiimide.

Methods of Making

Figure 9:
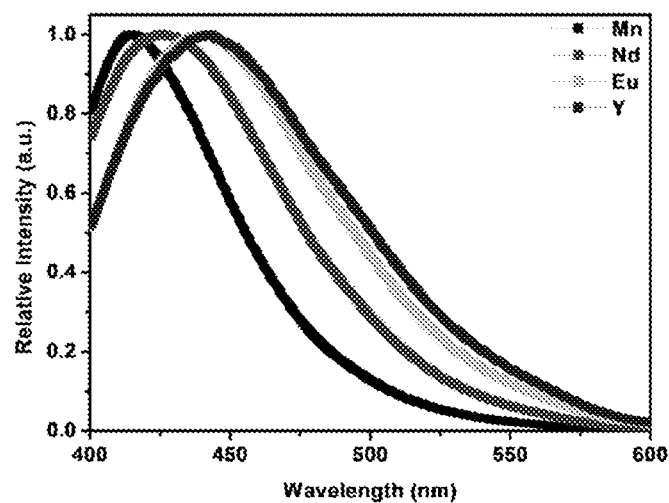
FIG. 9 shows the fluorescent spectra of metal-containing C-dots.

The disclosed M@C-dots can be prepared by calcining a metal with a chelator. An exemplary chelator that can be calcined with the metal is diethylenetriaminepentacetate (DTPA). DTPA can form complexes with a wide range of transition metals, especially Gd. By calcining the corresponding metal-DTPA complexes, metal-encapsulated M@C-dots can be produced. This method was tested with complexes formed between DTPA and $Mn^{2+}$, $Ni^{2+}$, $Co^{2+}$, $Zn^{2+}$, $Fe^{3+}$, $Nd^{3+}$, $Y^{3+}$, and $Eu^{3+}$. In all the scenarios, metal-containing C-dots (FIG. 9) were obtained, indicating the generality of the method.

Other chelator can be calcined with the metal to produce the disclosed nanoparticles. Examples of such chelators include, but are not limited to, 1,4,7-triazacyclononane-1,4, 7-triacetic acid (NOTA), 1,4,7,10-tetraazacyclodode-cane-1,4,7,10-tetraacetic acid (DOTA), 1,4,8,11-tetraazacyclododenane-1,4,8,11-tetraacetic acid (TETA), 2,2'-(1,4,8, 11-tetraazabicyclo[6.6.2]hexadecane-4,11-diyl)diacetic acid (CB-TE2A), 3,6,9,15-Tetraazabicyclo[9.3.1]pentadeca-1 (15),11,13-triene-3,6,9-triacetic acid (PCTA), pendetide (GYK-DTPA), cyclohexyldiethylenetriaminepentaacetic acid (CHX-DTPA), 2-(4,7-biscarboxymethyl[1,4,7]triazacyclonona-1-yl-ethyl)carbonyl-methylamino]acetic acid (NETA), diethylene triamine pentaacetic acid (DTPA), desferrioxamine, nitrilotriacetate (NTA), DO3A, ethylenediammine, acetylacetonate, phenanthroline, oxalate, citric acid, bipyridine, cyanide, nitrite, acetonitrile, ethylenediamine tetraacetic acid (EDTA), ethylene glycol tetraacetic acid (EGTA), poly-1-lysine, polyethylenimine, and polyvinylpyrrolidone (PVP). Salts, derivatives, and functionalized versions of these chelators can also be used.

Formulations

While it can be possible for disclosed nanoparticles to be administered neat, it is also possible to present them as a pharmaceutical formulation. Accordingly, provided herein are pharmaceutical formulations which comprise one or more of the disclosed nanoparticles together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof Proper formulation is dependent upon the route of administration chosen. Any of the well-known techniques, carriers, and excipients can be used as suitable and as understood in the art; e.g., in Remington: The Science and Practice of Pharmacy, 21$^{st}$ Ed., Gennaro, Ed., Lippencott Williams & Wilkins (2003). The compositions and formulations disclosed herein can be manufactured in any manner known in the art, e.g., by means of conventional mixing, dissolving, granulating, drageemaking, levigating, emulsifying, encapsulating, entrapping or compression processes.

A nanoparticle as disclosed herein can be incorporated into a variety of formulations for therapeutic administration, including solid, semi-solid, or liquid forms. The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route can depend upon for example the condition and disorder of the recipient. The formulations can conveniently be presented in unit dosage form and can be prepared by any of the methods well known in the art of pharmacy. Typically, these methods include the step of bringing into association a compound or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

The disclosed nanoparticles can be formulated for parenteral administration by injection, e.g., by bolus injection or continuous infusion. Formulations for injection can be presented in unit dosage form, e.g., in ampoules or in multidose containers, with an added preservative. The compositions can take such forms as suspensions, solutions or emulsions in oily or aqueous vehicles, and can contain formulatory agents such as suspending, stabilizing and/or dispersing agents. The formulations can be presented in unit-dose or multi-dose containers, for example sealed ampoules and vials, and can be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Formulations for parenteral administration include aqueous and non-aqueous (oily) sterile injection solutions of the active compounds which can contain antioxidants, buffers, bacteriostats and solutes which render the formulation isotonic with the blood of the intended recipient; and aqueous and non-aqueous sterile suspensions which can include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions.

Methods of Using

The disclosed nanoparticles have properties that can afford them uses as optical, MRI, fluorescence, photoacoustic imaging probes. The disclosed nanoparticles can also be used in therapy (drug delivery, gene delivery, photodynamic therapy), catalysis, energy, and electronics applications.

In a specific example, the disclosed nanoparticles can be used a MRI/fluorescence dual modal imaging probes. For example, the disclosed nanoparticles, or formulations containing them, can be used as imaging agents to visualize cancerous tissues, e.g., tumors. In one aspect, disclosed herein is a method of detecting cancer in vivo comprising administering a nanoparticle (e.g., Gd@C-dot) as disclosed herein to an individual and detecting a fluorescent signal and/or magnetic resonance signal. Also, a region of interest in the individual can be imaged using a fluorescence reflectance imaging system (such as the F-Pro from Bruker), which is fitted with multiple band pass filters for excitation and emission.

In recent years, many new fluorescence imaging systems, such as endoscopes (Hsiung et al., Nat Med 14:454 (2008); Funovics et al., Mol Imaging 2:350 (2003)), wide-field video cameras (Knapp et al., European urology 52:1700 (2007); van Dam et al., Nat Med 17:1315 (2011)), and goggles (Liu et al., Surgery 149:689 (2011); Wang et al., J Biomed Opt 15:020509 (2010)), have been developed. Any of these systems can be used to detect the fluorescent signal, or lack thereof, in an individual to whom the disclosed nanoparticles have been administered. Further, the development of the fluorescence can be followed using a near infrared video camera (e.g., Fluoptics).

The disclosed nanoparticles can also be used as MR imaging probes. The nanoparticles disclosed herein can be used to detect/image a variety of other cancers. Examples of cancer types detectable by the compounds and compositions disclosed herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Specific cancers contemplated for imaging include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Optical measurements were performed at room temperature under ambient air conditions. UV-Vis absorption spectra were recorded on a Shimdzu 2450 UV-Vis spectrometer. Photoluminescence (PL) measurements were performed on a Hitachi F-7000 fluorometer. Fourier transform infrared (FT-IR) spectra were recorded on a Nicolet iS10 FT-IR Spectrometer. The PL quantum yield (QY) was estimated using quinine sulfate in 0.1 M $H_2SO_4$ (literature quantum yield: 58% at 354 nm excitation) as a reference standard, which was freshly prepared to reduce the measurement error. The formula used for QY measurements is as follows:

$$(QY)_{sm} = (QY)_{st} \times [(PL_{area}/OD)_{sm}/(PL_{area}/OD)_{st}] \times \eta^2_{sm}/\eta^2_{st}$$

where Sm indicates the sample, St indicates the standard, $\eta$ is the refractive index of the solvent, and PL area and OD are the fluorescence area and absorbance value, respectively. TEM and HR-TEM samples were prepared by dispersing the sample onto carbon-coated copper grids with the excess solvent evaporated. The TEM/HR-TEM overview images were recorded using a FEI Tecnai20 transmission electron microscope operating at 200 kV. Energy Dispersive Spectroscopy (EDS) and element mapping was characterized using Hitachi HD2000 Dedicated Scanning Transmission Electron Microscope (STEM). Dynamic light scattering (DLS) analysis was performed on a Zetasizer Nano S90 size analyzer (Malvern Corp, U.K.). Fluorescence images were acquired on an Olympus X71 fluorescence microscope (ex/em: 360/420 nm).

Example 1

Gd@C-Dot Synthesis and Characterization

Gadolinium-DTPA (gadopentetic acid which is a complex of gadolinium with diethylenetriaminepentacetate) was dried on a crucible and then calcined at 300 ° C. for 2 h in the air. This yielded black foam-like powder. The raw products were dispersed in water and subjected to centrifugation using centrifugal filter units (Millipore filter units: MWCO 100K, 3K), which removed aggregations of nanoparticles and unreacted precursors, respectively. The soluble portion through the filter was collected. The yielded Gd@C-dots were spherical, with an average size of about 12 nm and relatively narrow size distribution (FIG. 1, panels (a) and (b)). High-resolution TEM (FIG. 1, panel (c)) found low diffraction contrast and no obvious lattice fringes with the particles, indicating that the carbon was amorphous. This correlates with previous observations that calcination at low pressure typically yields amorphous structures (Bourlinos et al., *Small* 2008, 4(4):455-458; Chen et al., *Theranostics* 2013, 3(9):650-657). Elemental mapping revealed that Gd was distributed evenly within the carbon particles (FIG. 1, panel (d)) (EDX pattern of Gd@C-dots as calculated by EDX software: C K 50.20%; O K 20.09%, N K 10.9%, Cu K12.82%, Gd L 6.71% =100%). The distribution pattern was also observed by scanning transmission electron microscopy (STEM) on a single C-dot particle (FIG. 1, panel (e)), showing that Gd was well encased within the carbon shell (FIG. 1, panel (f)).

Figure 6:
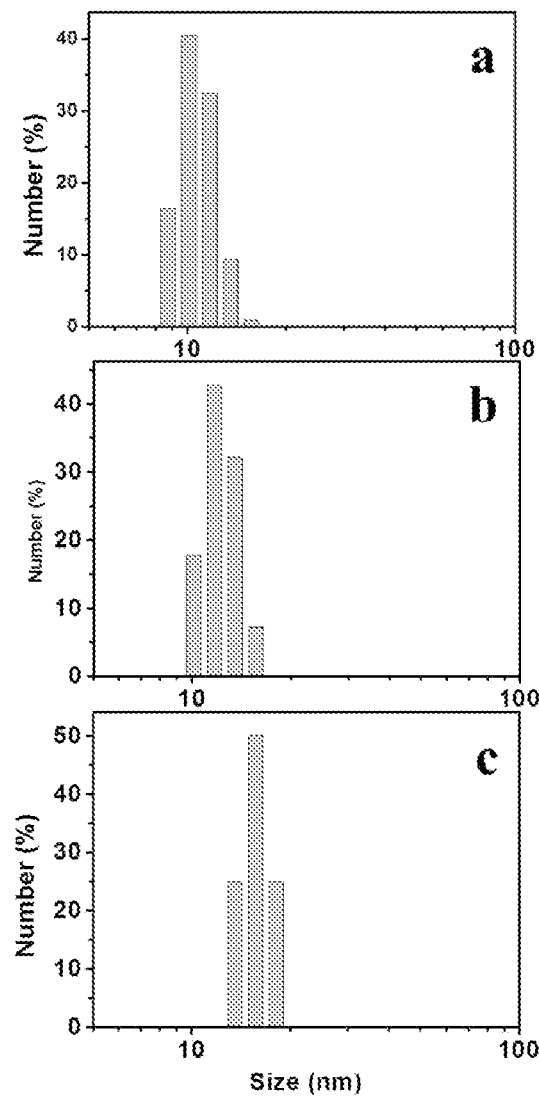
FIG. 6 shows the size distribution analysis of Gd@C-dots (panel (a)), RGD-Gd@C-dots (panel (b)), and Gd@C-dots in FBS (panel (c)) for 24 h.
Figure 7:
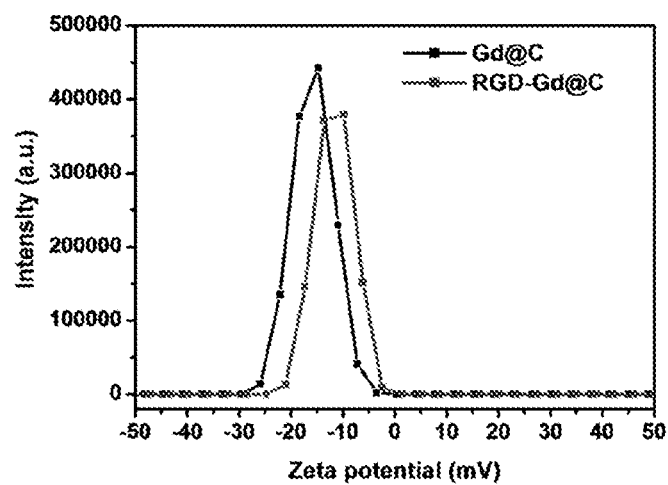
FIG. 7 shows the Zeta potentials of Gd@C-dots and RGD-Gd@C-dots.
Figure 8:
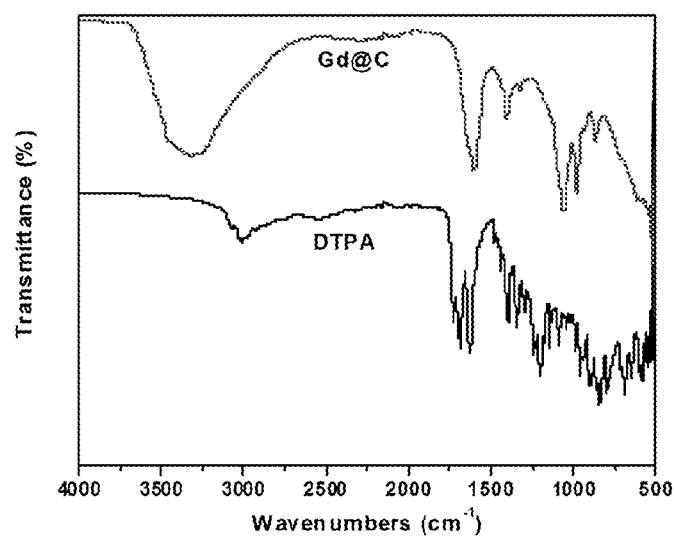
FIG. 8 shows the FTIR spectra of Gd@C-dots and DTPA.

The as-synthesized Gd@C-dots were highly dispersible in aqueous solutions, maintaining colloidal stability for months without visible precipitation. Dynamic light scattering (DLS) analysis showed a single narrow peak at about 12 nm, which is well correlated with the TEM result (FIG. 1, panel (g), FIG. 6). The surface of Gd@C-dots was slightly negatively charged (−16.4 ±0.6 mV, FIG. 1, panel (h), FIG. 7), attributed to carboxyl groups either inherited from the DTPA precursors and/or generated during the calcination. This is supported by FT-IR analysis, finding peaks at 3300 and 1600 $cm^{-1}$ that are characteristic absorptions of OH and C=O, respectively (FIG. 8) (Li et al., *Angew. Chem., Int. Ed.* 2013, 52(31):8151-8255;Bhunia et al., *Sci. Rep.* 2013, 3, 1473). Despite the charged surface, however, there was little size increase when the nanoparticles were incubated in the bovine serum (FIG. 6, panel (b)), indicating a minimal level of opsonization.

Figure 2:
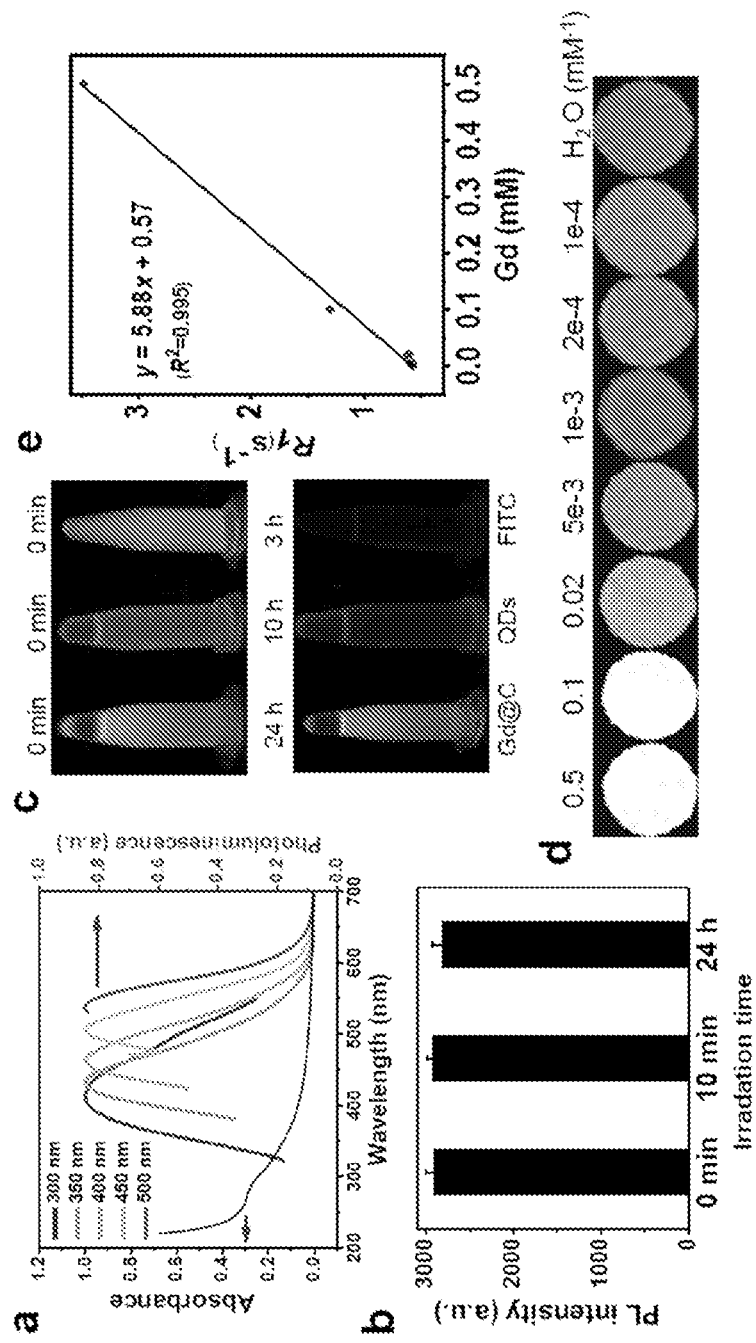

Gd@C-dots showed a broad absorption band between 200 to 500 nm, with a shoulder appearing at about 280 nm (FIG. 2, panel (a)). The spectrum resembles those published previously of pure C-dots (Chen et al., *Theranostics* 2013, 3(9):650-657; Bhunia et al., *Sci. Rep.* 2013, 3, 1473; Sun et al., *J. Am. Chem. Soc.* 2006, 128(24):7756-7757; Ding et al., *Acc. Chem. Res.* 2014, 47, 20-30). The Gd@C-dots are also highly fluorescent, and can be excited by light of a wide range of wavelengths to emit strong photoluminescence (FIG. 2, panel (a)). Such wavelength-dependent fluorescence is also similar to conventional C-dots (Bourlinos et al., *Small* 2008, 4(4):455-458; Li et al., *Angew. Chem., Int. Ed.* 2013, 52(31):8151-8255). Impressively, there was no drop of photoluminescence intensity of Gd@C-dots even after 24 hours of continuous UV illumination (FIG. 2, panel (b)). This photostability is vastly superior to organic dye molecules, and even better than CdSe/ZnS quantum dots (Michalet et al., *Science* 2005, 307(5709):538-544; Song et al., *Chem. Soc. Rev.* 2010, 39(11):4234-4243), both of which were completely bleached within hours of UV exposure (FIG. 2, panel (c)). The $T_1$ contrast ability was investigated on a 7T magnet with agarose samples of Gd@C-dots. Gd@C-dots showed an $r_1$ of 5.88 $mM^{-1}s^{-1}$ on a Gd basis (FIG. 2, panels (d) and (e)), which is significantly higher than Gd-DTPA (3.10 $mM^{-1}s^{-1}$) (Kim et al., *J. Am. Chem. Soc.* 2011, 133(9):2955-2961;Kalavagunta et al., *Contrast Media & Mol. Imaging* 2014, 9(2):169-176). The enhanced $r_1$ was mainly attributed to the increase in the rotational correlation time ($\tau_R$) as a result of binding Gd to a nanoparticle (Huang et al., *Curr. Top. Med. Chem.* 2013, 13(4):411-421).

Example 2

In Vitro Testing

Gd@C-dots were incubated in phosphate buffered saline of pH 5 or 7.4 at 37° C. for 72 h. At both pH values, no drop of luminescence intensity and negligible Gd leakage from the nanoparticles was observed over time (FIG. 3, panels (a) and (b)).

Gd@C-dots were also subjected to a cytotoxicity study with U87MG cells using standard MTT assays. The cells were first seeded in 96-well plates (1×$10^4$ cells per well). After 24 h, Gd@C-dots at different concentrations were added. Incubation was carried out for 24 h with or without 2.5 mM $CaCl_2$. To assess the particles' stability against transmetallation, which is the major cause of toxicity for conventional Gd contrast agents (Corot et al., *J. Magn. Reson. Imaging* 1998, 8(3):695-702), 2.5 mM Ca(II) was added into the incubation medium. No significant drop of cell viability was observed even at high nanoparticle concentrations (0-100 μg Gd/mL, FIG. 3, panel (c)). As a comparison, Gd-DTPA induced dramatic cell death under the same conditions with an $IC_{50}$ of 33.1 μg/mL (FIG. 3, panel (c)) (Wu et al., *Pharm. Res.* 2010, 27(7):1390-1397; Aime et al., *J. Magn. Reson. Imaging* 2009, 30(6):1259-1267).

Example 3

Conjugation of Gd@C-dots

Carboxyl groups on the Gd@C-dots surface offer a facile means to tether functional bio-species. As an example, c(RGDyK), a tumor targeting peptide, was conjugated onto the Gd@C-dots. A cyclic RGD derivative, c(RGDyK) holds strong binding affinity toward integrin $\alpha_v\beta_3$, a biomarker that is seen overexpressed on neoplastic blood vessels and many types of cancer cells (Ye et al., *Theranostics* 2011, 1:102-126). Specifically, Gd@C-dots were dispersed in a borate buffer (pH 8.3). Into the solution, carbodiimide (EDC) and N-hydroxysuccinimide (NHS) (10×) in DMSO was added, and the mixture was magnetically stirred for 30 min. The intermediate was purified by centrifugation, and redispersed in PBS (pH 7.4). Into the solution, c(RGDyK) in DMSO (20×) was added and the mixture was incubated for 2 h with gentle agitation. The product was collected using a centrifugal filtration unit (Millipore filter unit: MWCO 3K) and redispersed in PBS (pH=7.4). After the coupling, the nanoparticles' zeta potential increased slightly to −12.0±0.4 mV, and the size to about 16.0 nm (FIG. 6, panel (c)).

The targeting specificity of the c(RGDyK) conjugated Gd@C-dots (hereafter referred to as RGD-Gd@C-dots) was investigated with U87MG cells, which are integrin $\alpha_v\beta_3$ positive. U87MG cells were grown in a petri dish of a sterile glass bottom at 37° C. in 5% $CO_2$. Cells were incubated in 1 mL media containing Gd@C-dots (50 μg) with and without the presence of c(RGDyK) (1 mg) for 1 hour. Cells were washed three times with PBS (pH 7.4), and then imaged under an Olympus X71 fluorescence microscope. For MRI studies, $10^5$ cells treated under similar conditions were collected in 300 μL PCR tubes and subjected to $T_1$-weighted MRI.

Figure 3:
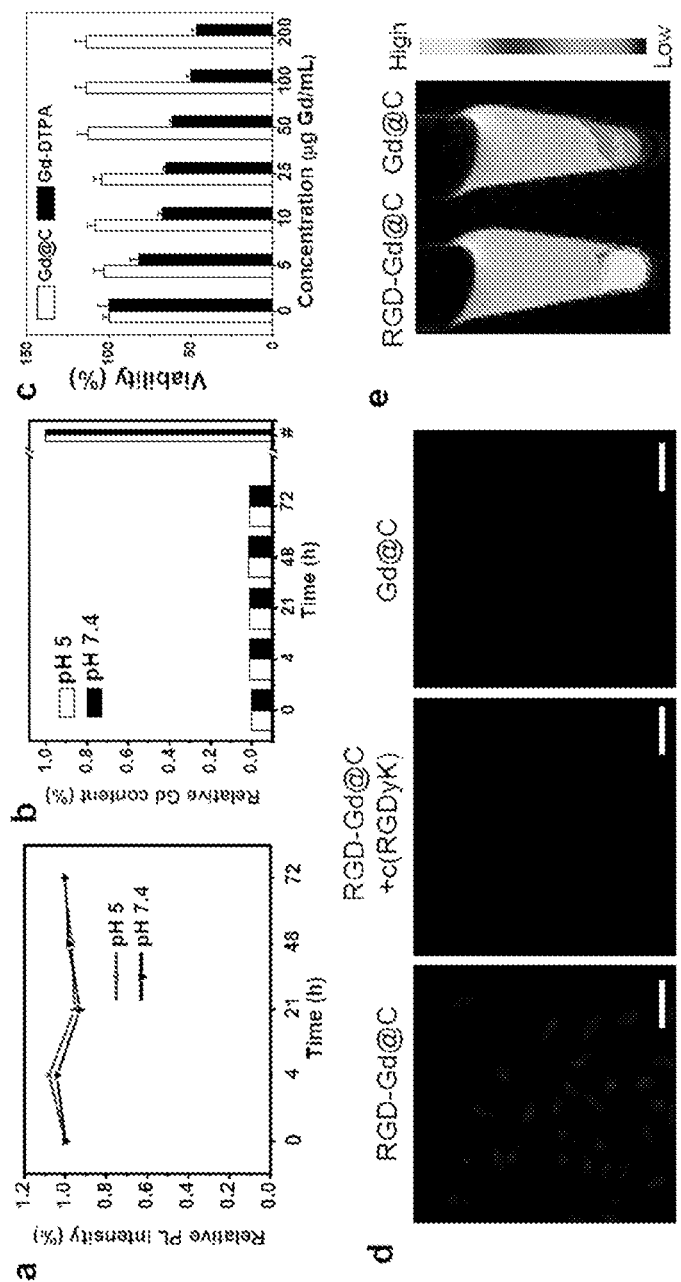

After 30 min incubation, there was a high level of nanoparticle uptake (ex/em: 360/460 nm), with many signals concentrated in the cell endosomes/lysomes (FIG. 3, panel (d)). The cell uptake was dramatically suppressed when Gd@C-dots were co-incubated with free c(RGDyK) (30×), indicating that the uptake was mostly mediated by RGD-integrin interaction. Such difference in cell uptake was also discerned by MRI. FIG. 3, panel (e), shows a $T_1$-weighted MR image of 105 U87MG cells that had been incubated with either RGD-Gd@C-dot or Gd@C-dots. Compared to the control, significantly enhanced signals were observed in cells incubated with RGD@C-dots (FIG. 3, panel (e)).

Example 4

In Vivo Testing

Animal studies were performed according to a protocol approved by the Institutional Animal Care and Use Committee (IACUC) of University of Georgia. Before in vivo experiments, the Gd@C-dots and RGD-Gd@C-dots were filtered through sterilized membrane filters (pore size 0.22 μm) and stored in sterilized vials. For in vivo MRI studies, whole body transverse images of normal athymic nude mice were first acquired. The mice were then intravenously (i.v.) injected with 100 μL Gd@C-dots and RGD-Gd@C-dots (0.8 mg Gd/kg). Transverse and coronal $T_1$-weighted MR images were acquired at 10, 30, 45 min, 60 min and 4 h post the nanoparticle injection (p.i.). The images were acquired using the following parameters: TR/TE=500/12 ms, field-of-view (FOV)=70×70 $mm^2$, matrix size=256×256, slice=4, and thickness=1 mm.

Figure 4:
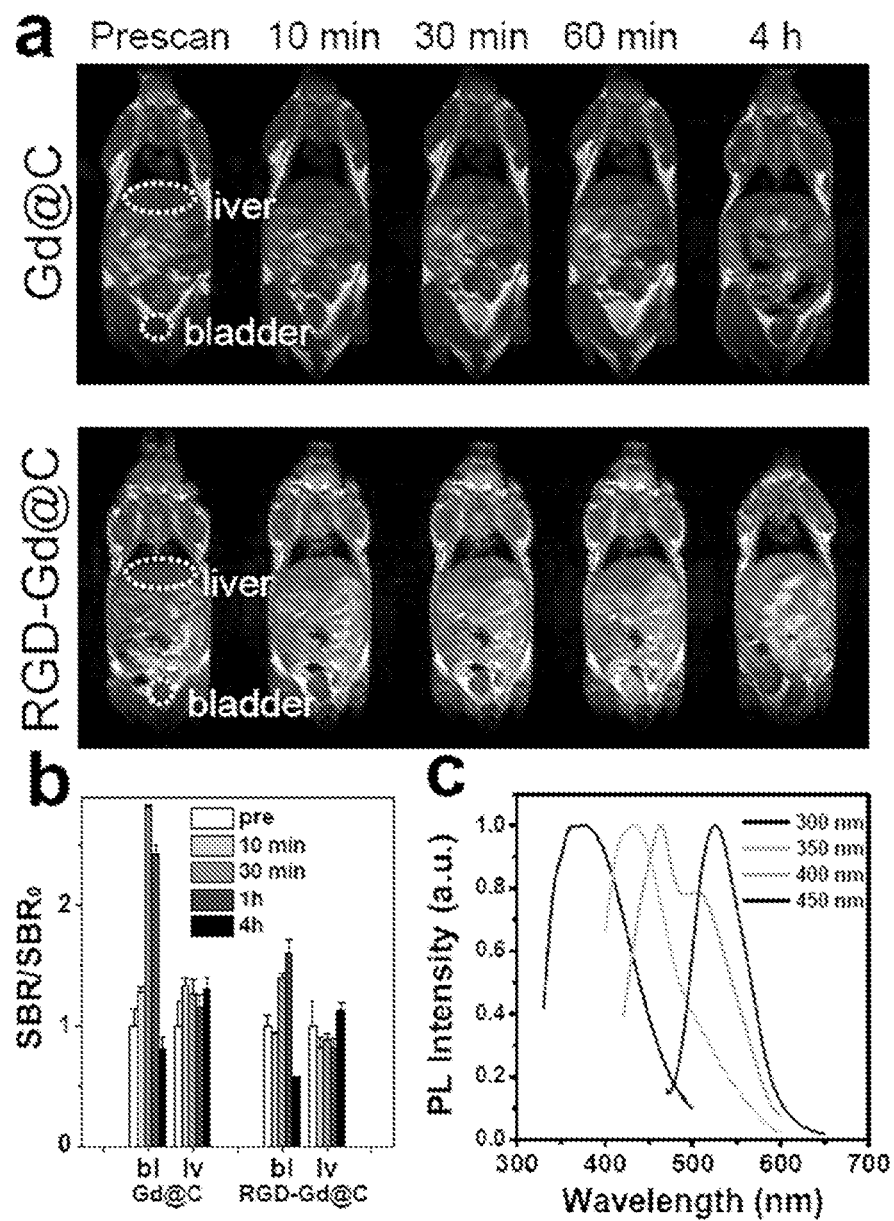

There was an initial increase of signals, followed by a signal decay starting from 60 min. After 4 h, all the signals had subsided to the pre-injection levels, indicating efficient clearance of Gd@C-dots from the body (FIG. 4, panel (a)). Unexpectedly, the signal change in the liver was found to be small throughout the course of the experiment (FIG. 4, panels (a) and (b)). Instead, there was a dramatic increase of signals in the bladder, indicating that most of the nanoparticles were excreted through renal clearance. Similar pharmacokinetics was observed with animals injected with RGD-Gd@C-dots (FIG. 4, panel (a) and (b)).

To validate, urine was collected from the animals about 60 min after the particle injection, and by centrifuging, nanoparticles were separated from the rest of the sample. Subsequent analysis found a large amount of Gd (by inductively coupled plasma mass spectroscopy, or ICP-MS) in the nanoparticle fragment, along with photoluminescence that was characteristic of C-dots (FIG. 4, panel (c)). On the other hand, no Gd was detected in the rest of the sample. This result confirmed the renal clearance of Gd@C-dots, and that the Gd was still encapsulated within the carbon shell at the time of excretion.

RGD-Gd@C-dots were also tested as tumor imaging probes in U87MG tumor-bearing mice. Tumor models were developed in 5-6 week athymic nude mice (Harlan) by subcutaneous implantation of $10^6$ human glioblastoma U87MG cells suspended in 100 μL of serum-free DMEM to the right lower flank of a mouse. Imaging studies were conducted 3-4 weeks later. Specifically, the tumor-bearing mice were intravenously injected with Gd@C-dots and RGD-Gd@C-dots (3.2 mg Gd/kg). Transverse and coronal $T_1$-weighted images were acquired at 15, 30, 60, 120, and 240 min post injection using the following parameters: TR/TE=500/12 ms, field-of-view (FOV)=70×70 $mm^2$, matrix size=256×256, slice=4, thickness=1 mm. To quantify the signal change, the signal-to-background ratio (SBR) was calculated by finely analyzing regions of interest (ROIs) of the MR images and calculating the values of $SBR/SBR_0$ to represent the signal changes. Signal intensity (SI) of normal live, kidney, brain, and muscle were measured before and after injection of Gd@C nanoparticles. The mean SI measurements of 3 mice per group were used for statistical analysis. Because of slight changes in the position of the mice at different imaging stages, pre and post ROIs were determined manually on each image as reproducible as possible. For each animal, 3-5 ROIs were selected to measure the SI of the liver, kidney, brain and muscle. The SBR values were calculated according to $SBR=SI_{organ}/SI_{muscle}$ for coronal plane, and $SBR/SBR_0=SI_t/SI_0$ for transverse plane. In a control group, Gd@C-dots at the same Gd dose were injected.

Figure 5:
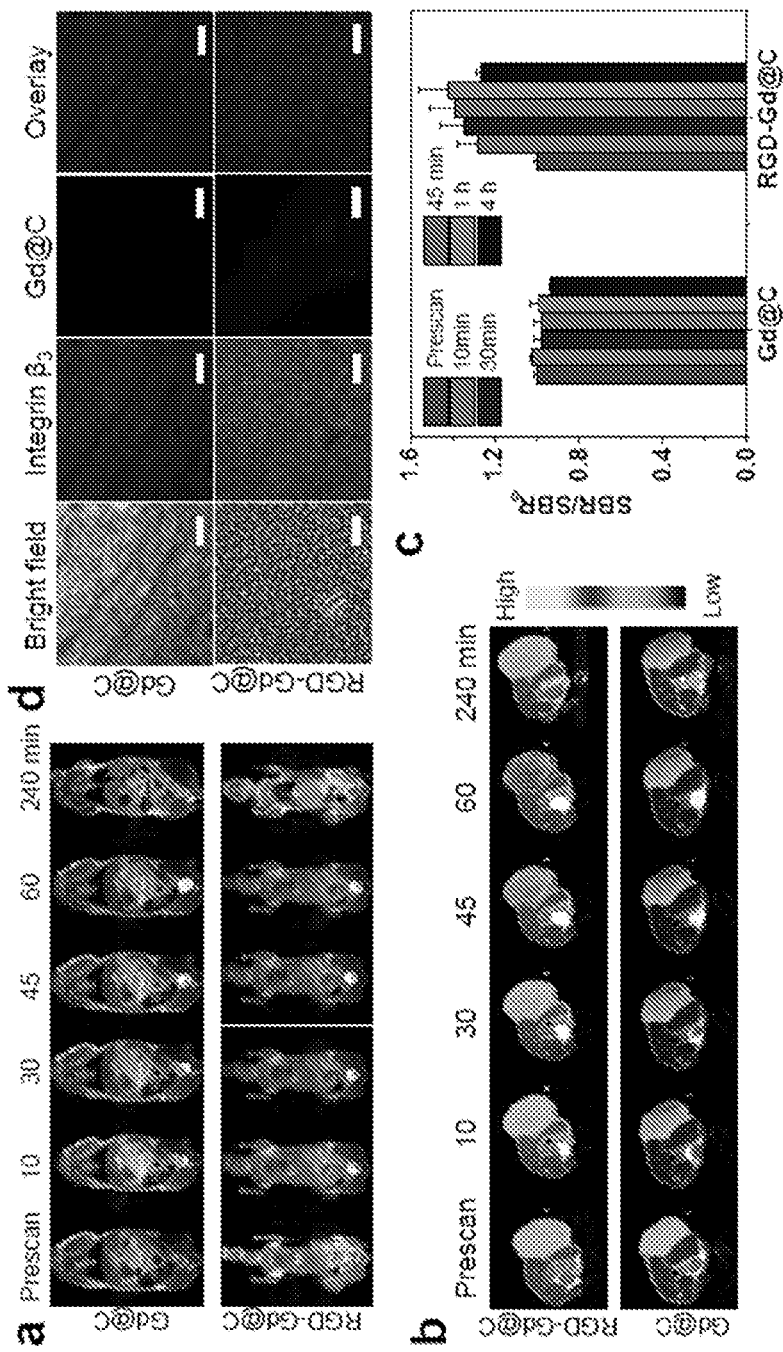

Similar to the above experiment, there was fast renal clearance of RGD-Gd@C-dots, evidenced by strongly enhanced intensities in the bladder (FIG. 5, panel (a)). After 4 h, signals in the normal tissues had receded to the normal level for both RGD-Gd@C-dots and Gd@C-dots injected animals. However, there was a signal enhancement in tumors of 42.6±0.08% in animals injected with RGD-Gd@C-dots compared to those injected with Gd@C-dots (FIG. 5, panels (b) and (c)). This retention of particles in tumors was attributed to RGD-integrin interaction, which was confirmed by immunofluorescent studies that found good overlap between RGD-Gd@C-dots (ex/em: 360/460 nm) and positive integrin $\beta_3$ staining (FIG. 5, panel (d)).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A nanoparticle, comprising: gadolinium encapsulated in an amorphous carbon shell, wherein the shell comprises carboxyl groups and wherein the average diameter of the nanoparticle is from about 2 nm to about 34 nm.

2. The nanoparticle of claim 1, wherein the gadolinium is Gd(III).

3. The nanoparticle of claim 1, wherein the average diameter is from about 10 nm to about 14 nm.

4. The nanoparticle of claim 1, wherein the average diameter is about 12 nm.

5. The nanoparticle of claim 1, wherein the nanoparticle has a $r_1$ relaxivity of from about 0 to about 50 mM$^{-1}$s$^{-1}$.

6. The nanoparticle of claim 1, wherein the nanoparticle has a $r_1$ relaxivity of from about 5 to about 25 mM$^{-1}$s$^{-1}$.

7. The nanoparticle of claim 1, wherein the nanoparticle has a quantum yield of from about 0 to about 80%.

8. The nanoparticle of claim 1, wherein the nanoparticle has a quantum yield of from about 15 to about 50%.

9. The nanoparticle of claim 1, wherein the nanoparticle is conjugated to a targeting moiety.

10. The nanoparticle of claim 1, wherein the nanoparticle is conjugated to a cyclic RDG peptide.

11. The nanoparticle of claim 1, wherein the nanoparticle is conjugated to Herceptin, Avastin, Erbitux, doxorubicin, methotrexate or paclitaxel, or polyethylenimine.

12. A method of imaging cancer in a subject, comprising:
   administering to the subject the nanoparticle of claim 1; and detecting a fluorescent and/or magnetic resonance signal from the cancer.

13. A method of making the nanoparticle of claim 1, comprising:
   calcining gadolinium with a chelator.

14. The method of claim 13, wherein the chelator is diethylenetriaminepentacetate.

15. The method of claim 13, wherein the chelator is 1,4,7-triazacyclononane-1,4,7-triacetic acid (NOTA), 1,4,7, 10-tetraazacyclodode-cane-1, 4, 7,10-tetraacetic acid (DOTA), 1,4,8,11-tetraazacyclododenane-1,4,8,11-tetraacetic acid (TETA), 2,2'-(1,4,8,11-tetraazabicyclo[6.6.2] hexadecane-4,11-diyl)diacetic acid (CB-TE2A), 3,6,9,15-Tetraazabicyclo[9.3.1]pentadeca-1(15),11,13-triene-3,6,9-triacetic acid (PCTA), pendetide (GYK-DTPA), cyclohexyldiethylenetriaminepentaacetic acid (CHX-DTPA), 2-(4,7-biscarboxymethyl[1,4,7]triazacyclonona-1-yl-ethyl)carbonyl-methylamino]acetic acid (NETA), diethylene triamine pentaacetic acid (DTPA), desferrioxamine, nitrilotriacetate (NTA), DO3A, ethylenediammine, acetylacetonate, phenanthroline, oxalate, citric acid, bipyridine, cyanide, nitrite, acetonitrile, ethylenediamine tetraacetic acid (EDTA), ethylene glycol tetraacetic acid (EGTA), poly-1-lysine, polyethylenimine, or polyvinylpyrrolidone (PVP), or any salt, derivative, functionalized analog, or mixture of these.

16. A nanoparticle, comprising: a metal encapsulated in an amorphous carbon shell, wherein the shell comprises carboxyl groups and wherein the average diameter of the nanoparticle is from about 2 nm to about 34 nm.

17. The nanoparticle of claim 16, wherein the metal is Fe, Mn, Ti, Co, Ni, Cu, Zn, Ga, Ge, Y, Au, Ag, Pt, Cr, Cd, Pb, Ce, Eu, Dy, Tb, Ho, Er, Tm, or Yb.

18. A method of making the nanoparticle of claim 16, comprising:
   calcining a metal with a chelator.

19. The method of claim 18, wherein the metal is Fe, Mn, Ti, Co, Ni, Cu, Zn, Ga, Ge, Y, Au, Ag, Pt, Cr, Cd, Pb, Ce, Eu, Dy, Tb, Ho, Er, Tm, or Yb.

20. The method of claim 18, wherein the chelator is diethylenetriaminepentacetate, 1,4,7-triazacyclononane-1,4, 7-triacetic acid (NOTA), 1,4,7,10-tetraazacyclodode-cane-1, 4, 7,10-tetraacetic acid (DOTA), 1,4,8,11-tetraazacyclododenane-1,4,8,11-tetraacetic acid (TETA), 2,2'-(1,4,8, 11-tetraazabicyclo[6.6.2]hexadecane-4,11-diyl)diacetic acid (CB-TE2A), 3,6,9,15-Tetraazabicyclo[9.3.1]pentadeca-1 (15),11,13-triene-3,6,9-triacetic acid (PCTA), pendetide (GYK-DTPA), cyclohexyldiethylenetriaminepentaacetic acid (CHX-DTPA), 2-(4,7-biscarboxymethyl[1,4,7]triazacyclonona-1-yl-ethyl)carbonyl-methylamino]acetic acid (NETA), diethylene triamine pentaacetic acid (DTPA), desferrioxamine, nitrilotriacetate (NTA), DO3A, ethylenediammine, acetylacetonate, phenanthroline, oxalate, citric acid, bipyridine, cyanide, nitrite, acetonitrile, ethylenediamine tetraacetic acid (EDTA), ethylene glycol tetraacetic acid (EGTA), poly-1-lysine, polyethylenimine, or polyvinylpyrrolidone (PVP) or any salt, derivative, functionalized analog, or mixture of these.

\* \* \* \* \*